United States Patent [19]

Vadekar et al.

[11] 4,387,258
[45] Jun. 7, 1983

[54] SELECTIVE HYDROGENATION USING PALLADIUM/PLATINUM ON CRYSTALLINE SILICA POLYMORPH/SILICALITE/HIGH SILICA ZEOLITE

[75] Inventors: Mohan Vadekar, Wassenaar, Netherlands; Harry E. Robson, Baton Rouge, La.

[73] Assignee: Exxon Research & Engineering Co., Florham Park, N.J.

[21] Appl. No.: 342,719

[22] Filed: Jan. 25, 1982

[30] Foreign Application Priority Data

Jan. 28, 1981 [GB] United Kingdom ............... 8102514

[51] Int. Cl.³ .................. C07C 5/14; C07C 5/06; C07C 5/16; C07C 5/08
[52] U.S. Cl. .................. 585/259; 585/260; 585/273; 585/275; 252/455 Z
[58] Field of Search ............ 585/259, 262, 273, 275; 252/460, 476, 455 Z

[56] References Cited

U.S. PATENT DOCUMENTS

| | | | |
|---|---|---|---|
| 4,061,724 | 12/1977 | Grose et al. | 252/455 Z |
| 4,309,276 | 1/1982 | Miller | 252/455 Z |
| 4,329,530 | 5/1982 | Irine et al. | 585/259 |
| 4,347,392 | 8/1982 | Cosyns et al. | 585/259 |

FOREIGN PATENT DOCUMENTS

| | | | |
|---|---|---|---|
| 35807 | 9/1981 | European Pat. Off. | 252/455 Z |
| 1418198 | 9/1969 | Fed. Rep. of Germany | 585/259 |

OTHER PUBLICATIONS

Bibby et al., Nature, 280, 664 (1979).
Wu et al., J. Phys. Chem., 83, 2778 (1979).
Olson, et al., J. Catalysis, 61, 390 (1980).
Anderson et al., J. Catalysis, 58, 114 (1979).

*Primary Examiner*—Delbert E. Gantz
*Assistant Examiner*—A. Pal
*Attorney, Agent, or Firm*—Rebecca Yablonsky

[57] ABSTRACT

Palladium or platinum is deposited on a low acidity silica polymorph/silicalite/high silica zeolites to yield a supported catalyst particularly useful in the hydrogenation of acetylenes and diolefins. The catalyst has a decreased tendency to promote polymerization which causes fouling than previously used alumina catalysts.

20 Claims, 4 Drawing Figures

FIG. 1

| KEY: | REACTION TEMP. (°C) | CATALYST |
|---|---|---|
| △ | 75 | EXAMPLE 3 |
| ▲ | 75 | EXAMPLE 3 |
| ■ | 75 | EXAMPLE 3 |
| ○ | 75 | EXAMPLE 1 |
| ⬡ | 25 | EXAMPLE 1 |

FIG. 2

KEY:
△ REACTION TEMPERATURE = 75°C
○ REACTION TEMPERATURE = 75°C CATALYST REGENERATED IN AIR AT 550°C
▲ REACTION TEMPERATURE = 75°C
● REACTION TEMPERATURE = 25°C, CATALYST REGENERATED IN AIR AT 550°C

FIG. 4

SELECTIVE HYDROGENATION USING PALLADIUM/PLATINUM ON CRYSTALLINE SILICA POLYMORPH/SILICALITE/HIGH SILICA ZEOLITE

The present invention relates to the selective hydrogenation of unsaturated hydrocarbon feeds using catalysts comprising a catalytically-active metal on a crystalline silica support, and especially to the hydrogenation of acetylenic and diolefinic compounds to monoolefins.

Steam cracked hydrocarbon streams are important as a source or polymerization grade olefins such as ethylene, propylene and butylenes and they are also used as a source of aromatics hydrocarbons. Thus streams also contain significant amounts of diolefins and acetylenes which must be removed by selective hydrogenation as their presence would cause problems in subsequent processing of the streams.

It has been common practice to remove these acetylenic and diolefinic compounds by selective hydrogenation over a supported palladium catalyst, the support generally being alumina. The use of alumina supports, however, creates a problem in that as a competing reaction to the desired hydrogenation corresponding monoolefins, the diolefins and acetylenes tend to undergo oligomerization on the carrier alumina surface, to produce higher molecular weight species. The latter often remains on the catalyst surface as "green oils" or solid polymers which gradually fill the pores of the catalyst and in turn effectively block both the diffusion of the reactive species (diolefins, acetylenes and hydrogen) to the catalyst and the effusion from the catalyst of the formed hydrogenated products. This fouling of the catalyst severely limits the long term operation of the hydrogenation process leading to shorter run-lengths and expensive regenerations.

The polymerization of the diolefins/acetylenes is thought to be catalysed by Lewis acid sites on the $Al_2O_3$ catalyst surface. Furthermore, the wide range of pore sizes found in amorphous aluminas leads to rapid plugging of the smaller pores when polymers are formed. Attempts have been made to overcome these problems by optimizing the BET surface area of the aluminas to control acidity and by choosing wide pore aluminas, but these attempts to improve long term operation have met with limited success.

This invention seeks to provide a hydrogenation catalyst suitable for long term operation. The invention resides in the use in the catalyst of a carrier with inherently low total acidity and a regular pore structure which serves to minimize the loss in efficiency resulting from polymer fouling.

The invention provides a method of selectively hydrogenating an unsaturated hydrocarbon feed to convert alkynes and dienes to alkenes containing a single olefinic double bond, in which the feed is contacted with hydrogen over a catalyst comprising palladium or platinum supported on a crystalline silica polymorph having a total acidity not greater than $40\mu$ mole/g as measured by pyridine adsorption at 300° C.

The silica polymorph may be a crystalline silica with a structure analogous to a zeolite or a highly siliceous zeolite, but in each case having very low levels of metal substitution within the tetrahedral silica framework and having the desired level of total acidity. Preferred silica polymorphs are those in which the ratio of silicon to modifying elements such as aluminium in the tetrahedral framework is greater than 500, and more preferably greater than 5000 and approaches infinity.

The core material may contain small amounts of other elements as impurities which do not form part of the tetrahedral silica structure and do not contribute to the catalytic activity of the silica. For example, suitable silicas may contain aluminium impurities in amounts of up to 0.3 wt%, where this is occluded in a separate phase, and have little catalytic or acidic activity. Preferably, however, the total aluminium content of the carrier is less than 0.2 wt%.

The carriers for use in the invention must have a total acidity of not greater than $40\mu$ moles/g as defined hereinbefore. Preferably the catalyst carrier has an acidity of not greater than $30\mu$ moles/g, more preferably not greater than $20\mu$ moles/g. By chemical treatment of the carrier it is possible to achieve yet lower acidity—of 0 to $15\mu$ moles/g—or even basic character. The silica polymorph preferably has, after calcination in air for at least one hour at 600° C., a mean refractive index of $1.39\pm0.01$ and a specific gravity at 25° C. of $1.70\pm0.05$. In one preferred form the polymorph has an X-ray powder diffraction pattern in which the six strongest d-values are:

$11.1\pm0.2$ Å
$10.0\pm0.2$ Å
$3.85\pm0.07$ Å
$3.82\pm0.07$ Å
$3.76\pm0.05$ Å
$3.72\pm0.05$ Å

This preferred silica polymorph is known as "silicalite", and is described in U.S. Pat. No. 4,061,724 assigned to Union Carbide Corporation.

The pore diameter of silicalite is in the range of from 5 to 6 Angstrom units and the pore volume is typically 0.18 ml/g determined by adsorption.

Silicalite may be prepared by the process described in U.S. Pat. No. 4,061,724 which consists of a hydrothermal crystallization from an aqueous reaction mixture containing a silica source and an alkylonium compound at pH 10-14 to form a hydrous precursor, followed by calcining the precursor. However, silicalite may also be prepared in the absence of alkonium compounds—for example, in a manner analogous to that described in U.K. Pat. No. 1,574,840 in respect of the related aluminosilicate zeolite known as "ELZ-105".

A second preferred form of silica polymorph, related to silicalite, has, in addition to the refractive index and specific gravity characteristics following calcination in air for at least an hour at 600° C. an adsorptive capacity for water vapour at 23° C. and a water vapour pressure of 4.6 mm Hg of less than 1 wt %, an infra-red spectrum which exhibits a substantial absence of absorption in the region 3700–3100 $cm^{-1}$, and an X-ray powder diffraction pattern containing at least the following d-values:

$11.1\pm0.2$
$10.0\pm0.2$
$9.75\pm0.1$
$3.85\pm0.04$
$3.82\pm0.04$
$3.71\pm0.02$
$3.62\pm0.02$ and an absence of reflections intermediate the reflections corresponding to d-spacings of $3.82\pm0.04$ Å and $3.71\pm0.02$ Å.

This second form of preferred silica polymorph is described and claimed in U.S. Pat. No. 4,073,865 assigned to Union Carbide Corporation. The polymorph may be prepared by the process as described in U.S. Pat. No. 4,073,865, which employs a reaction mixture having a pH below 11, preferably within the range of 7 to 11, more preferably 7.4 to 10, which in terms of moles of oxides contains from 150 to 1500 moles $H_2O$, from 13 to 50 moles $SiO_2$, from 2 to 12 moles of fluoride ion and from 0 to 20 moles, preferably 0 to 16 moles, $M_2O$ wherein M represents an alkali metal cation, each of the aforesaid reagents being present per mole of $Q_2O$ wherein Q represents a quaternary cation having the formula $(R_4X)+$, in which each R represents hydrogen or an alkyl group containing from 2 to 6 carbon atoms, and X represents phosphorus or nitrogen, heating the reaction mixture thus provided at a temperature of from 100° to 250° C. until a crystalline hydrated precursor is formed, usually about 50 to 150 hours, isolating said crystalline precursor and calcining same at a temperature of from 400° C. to 1000° C. The silic polymorph may, however, alternatively be prepared in the absence of the compound $Q_2O$.

The catalysts of the present invention preferably comprise from 0.05 to 1.0 wt% palladium or platinum based on the weight of the complete catalyst. Palladium is the preferred catalytically-active metal.

The amount of palladium or platinum incorporated in the catalyst of the invention is not crucial, but it has been found that if less than 0.05 wt % is present the catalytic activity is impaired. In general a palladium or platinum content of from 0.1 to 0.05% by weight of the catalyst is preferred. A catalyst of the invention including 0.3% by weight of palladium has been found to be particularly useful.

The platinum or palladium crystallites may have a diameter of from 10 to 2000 A and excellent results have been obtained using catalysts calculated (from metal surface area measurements) as having palladium crystallites of from 20 to 200 Å. However, the crystallite size is not normally measured, and it is sufficient if the metal component is well dispersed in the silica polymorph. Good dispersion of the metal results in disappearance from the x-ray diffraction pattern of the lines characteristic of the metal—2.25 Å for palladium and 2.27 Å for platinum.

The palladium may be introduced by depositing a palladium salt onto the silica polymorph followed by calcining and reduction. The palladium salt used must be capable of decomposing under the calcining conditions. The oxide formed is then reduced to metallic palladium.

The palladium salt may be, for example, a nitrate, lactate, acetate or chloride, and palladium acetate and palladium chloride are preferred. A variety of techniques are known for depositing the palladium salt upon the support, as would be appreciated by one skilled in the art. The procedure may be summarized as comprising adding the support to a solution of the salt, or vice versa, followed by drying and/or draining. The deposited palladium salt is calcined, preferably at a temperature in the range of from 300° to 450° C. for 16 hours.

The reduction of palladium oxide to metallic palladium is conveniently carried out by means of a hydrogen atmosphere preferably at a temperature of from 100° to 200° C. for a period of from 2 to 6 hours.

Other means of applying palladium to the silica support could be employed such as gas or vapour phase deposition, copelletizing, co-extrusion and ion exchange.

The selective hydrogenation of an unsaturated hydrocarbon feed using the catalyst of the invention may be carried out under the conventional conditions for this treatment, and it is believed to be within the competence of one skilled in the art to select appropriate hydrogenation conditions. By way of illustration only, it may be said that the unsaturated feed will usually be passed over the catalyst with hydrogen at an input temperature of from 25° to 150° C. and a pressure of from 5 to 45 atmospheres. Preferably the liquid hourly space velocity is from 0.5 to 6.

The following Examples are now presented, though only by way of illustration, to show certain aspects of the invention in more detail. Reference is made to the accompanying drawings, in which.

EXAMPLE 1

(a) Silica polymorph carrier

A silica polymorph was prepared for use as a carrier in the catalyst of the invention. The X-ray powder diffraction pattern for this polymorph gas as follows:

| d spacing (A) | Intensity |
| --- | --- |
| 11.26 | vs |
| 10.11 | vs |
| 8.15 | vw |
| 7.50 | vw |
| 7.38 | vw |
| 7.08 | vw |
| 6.97 | vw |
| 6.73 | w |
| 6.39 | w |
| 6.03 | m |
| 5.72 | w |
| 5.61 | m |
| 5.39 | vw |
| 5.17 | vw |
| 5.01 | w |
| 4.62 | w |
| 4.37 | w |
| 4.28 | w |
| 4.09 | vw |
| 4.02 | w |
| 3.86 | vs |
| 3.73 | s |
| 3.66 | m |
| 3.46 | w |
| 3.36 | vw |
| 3.32 | w |
| 3.27 | vw |
| 3.16 | vw |
| 3.05 | w |
| 2.99 | w |
| 2.88 | vw |
| 2.74 | vw |
| 2.68 | vw |
| 2.61 | vw |
| 2.60 | vw |
| 2.59 | vw |
| 2.57 | vw |
| 2.48 | vw |
| 2.40 | vw |
| 2.01 | vw |
| 2.00 | vw |

-continued

| d spacing (A) | Intensity |
| --- | --- |
| 1.96 | vw |
| 1.92 | vw |
| 1.87 | vw |

The silica polymorph was prepared using the following method: 476 g of silica sol (Ludox HS-40) were diluted with 100 ml of water. The formed solution was mixed with 130 ml of 20% (by wt) tetrapropylammonium hydroxide solution. To this mixture was added a solution of 33 g of sodium hydroxide in 100 ml of water to form a synthesis gel.

The gel was placed in two 250 ml polypropylene bottles provided with condensers which were heated in an oil bath for 7 days at 100° C. to bring about crystallization. The formed crystals were collected, washed and dried. Scanning Electron Photomicrographs showed the product to be in the form of spherical crystal aggregates with a particle size of 0.5 micron.

(b) Palladium deposition

The silica polymorph formed as a powder in step (a) was contacted with an aqueous solution of palladium acetate containing palladium in an amount corresponding to 0.3 wt % of the complete catalyst. The powder was shaken in the solution to ensure a uniform dispersion of the palladium salt, and then dried with agitation on a rotary evaporator.

The dried, impregnated powder was then calcined in a muffle furnace at 250° to 300° C. overnight to convert the palladium salt to palladium oxide.

The catalyst may be pelletised, then stored in the oxidised form and reduced to the metallic palladium form in situ when required. Alternatively the oxidised form of the catalyst may be pelletised and reduced to the metallic palladium form ready for use immediately on preparation. The reduction is carried out using a hydrogen atmosphere at a temperature of 100° to 150° C. for at least one hour.

EXAMPLE 2

Supported Palladium Catalyst

The procedure of Example 1(a) was repeated. The formed silica polymorph powder was then extruded with 15 wt% of a kaolin binder to form pellets, which were then impregnated, dried, calcined and reduced in the manner described in Example 1(b).

EXAMPLE 3

Supported Palladium Catalyst

The procedure of Example 1(a) was repeated except that palladium acetate was added to the crystallisation mixture in an amount corresponding to 0.3 wt % of palladium in the final catalyst. In this way the product of step (a) comprised a palladium salt deposited on a silica polymorph support. This product was dried, and then calcined and reduced in the manner described in Example 1(b).

EXAMPLE 4

Supported Platinum Catalyst

The procedure of Example 3 was repeated, but using platinum acetate in place of palladium acetate. A supported platinum catalyst containing 0.3 wt % platinum was prepared.

EXAMPLE 5

Selective Hydrogenation

The catalyst of Example 3 was compared with a commercially available palladium-on-alumina catalyst, designated Comparison I The characteristics of the two catalysts are indicated below in Table 1.

TABLE 1

| Catalyst | Comparison I | Example 3 |
| --- | --- | --- |
| Composition | | |
| - Palladium wt % (+0.03) | 0.3 | 0.3 |
| - Alumina purity wt %[1] | 99.5 | |
| - Sulfur wt % | 0.16 | — |
| Bulk density (kg/m$^3$) | 673 | 481 |
| Crush Strength (kg/m$^3$) | 192-240 | 80 |
| Surface Area (BET) m$^2$/g | 82 | 81 |
| Pore Volume cc/g | 0.50 | 0.21 |
| Acidity $\mu$moles/g[2] | | |
| Total | 35 | 40 |
| - Bronsted | 2 | 7 |
| - Lewis | 33 | 33 |

[1] Traces of other insignificant impurities.
[2] Measured by pyridine adsorption at 300° C. (total acidity) and lutidine adsorption (Lewis acidity). Bronsted acid equals total acidity minus Lewis acidity. The results are expressed as micromoles of base adsorbed per gram of catalyst carrier.

The catalyst were tested using a 12.5 mm tubular reactor to which was fed a stream cracked naphtha stream containing 70 wt % benzene and 2.5 wt % mixed diolefins together with a hydrogen stream, the hydrogen/hydrocarbon ratio being 90 Nm$^3$/m$^3$, and the LHSV being 6. The diolefin conversion at various reactor temperatures was determined by the UVK method monitoring UV absorbtion at 235$\mu$, this absorbtion being specific to diolefin. The results obtained are given in Table 2 and demonstrate the greater efficiency to be obtained by using the catalyst of the invention, even though the comparison alumina catalyst is of comparatively low acidity.

TABLE 2

| Catalyst (0.3 wt % Pd) | Temperature (°C.) | Diolefin Conversion (%) |
| --- | --- | --- |
| Example 3 | 25 | 96.8 |
| | 35 | 97.4 |
| | 50 | 97.4 |
| | 75 | 98.7 |
| Comparison I | 35 | 75.5 |
| | 50 | 80.0 |
| | 70 | 92.0 |

EXAMPLE 6

Selective Hydrogenation

The catalysts prepared in Examples 1 and 3 were compared in the selective hydrogenation of SCN feed containing diolefins.

The SCN feed contained approximately 78.5% benzene, and 11.3% diolefins, and to this was added 50 ppm a commercially-available inhibitor, Kerobit. 120 ml/hr of the feed were passed together with 11 l/hr hydrogen over the catalyst under test in a 12.5 mm tubular reactor at a pressure of 24 bar g and an LHSV of 6.0. The diolefin conversion was measured at 25° C. and 75° C. using the UVK method by measuring UV absorbtion of samples taken at 15 minute intervals. The results are shown graphically in FIG. 1, as percentage diolefin conversion against time.

Figure 1:
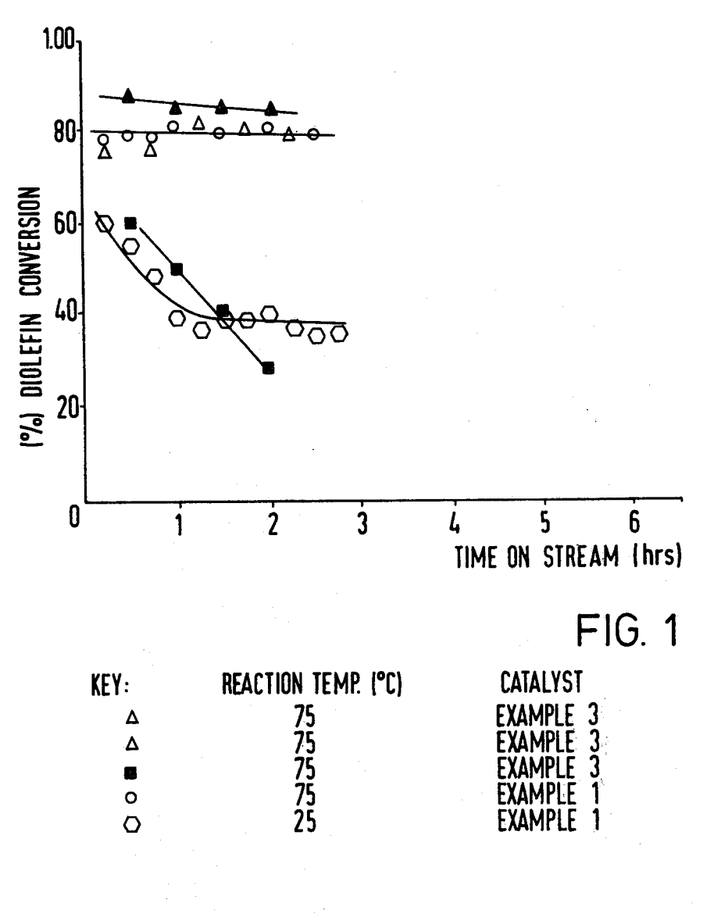
FIG. 1 is a graph of percentage diolefin conversion against reaction time for a supported palladium catalyst of the invention.

With the catalyst of Example 3 at 75° C. a steady state was reached of 80% conversion determined by UVK. A similar result was obtained for the catalyst of Example 1 at 75° C. In this case in addition to the relative UVK conversion of 80% a real diolefin conversion of 90 wt % was determined by gas chromatography. The mono-olefin conversion to saturates was 14 wt %. At 25° C. the UVK conversion over both catalysts was initally 60%. Over the catalyst of Example 3 the conversion continuously decreased whereas over the catalyst of Example 1 a steady state of 35–40% was reached. This indicated that impregnation resulted in a more stable catalyst than coprecipitation.

EXAMPLE 7

Selective Hydrogenation using a Supported Platinum Catalyst

Figure 2:
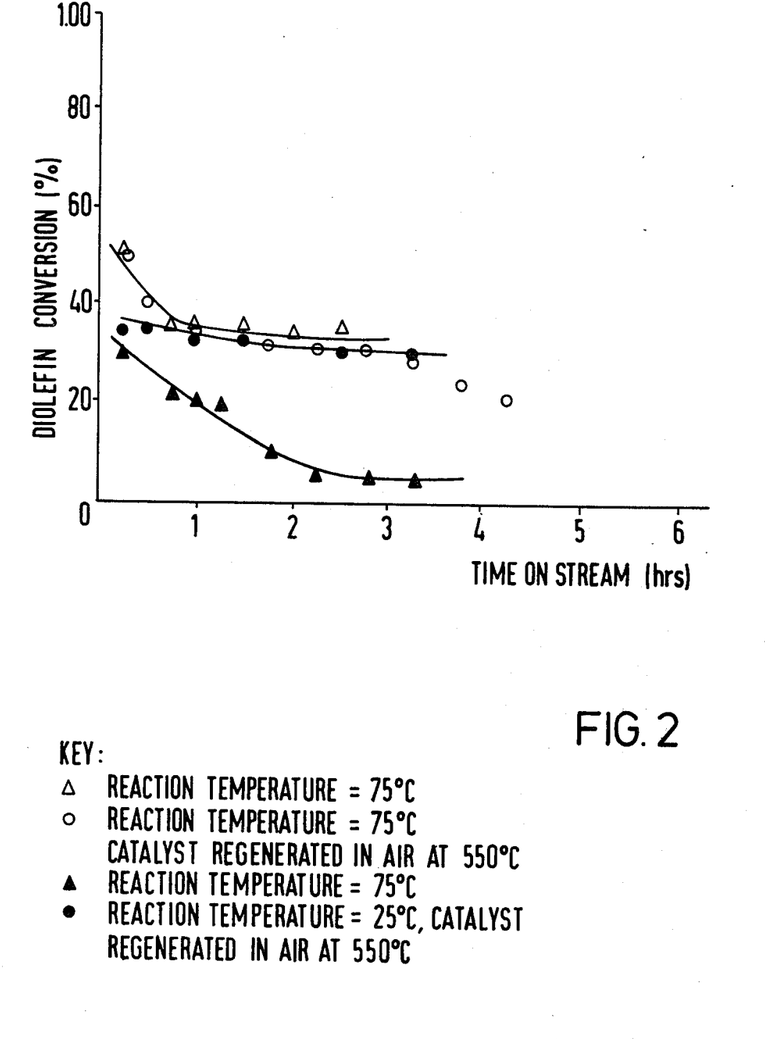
FIG. 2 is a similar graph to FIG. 1, but showing the results for a supported platinum catalyst of the invention.

The test procedure of Example 6 was repeated but using the catalyst of Example 4. The results are shown in FIG. 2, which is a graph of % diolefin conversion (determined by UVK) against time.

At 75° C. the steady state conversion is 35%. Regeneration of this catalyst at 550° C. to remove any coke formed during previous experiments resulted, especially at a reaction temperature of 25° C., in a more active and stable catalyst.

EXAMPLE 8

Selective Hydrogenation-long term test

The catalyst of Example 2 was tested over a period exceeding 100 hours and compared with 2 conventional palladium-on-alumina catalysts. The comparison catalysts were Comparison I (identified in Example 5) and Comparison II. Details of the catalyst of Example 2 and Comparison II are as follows:

TABLE 3

| Catalyst | Comparison II | Example 2 |
| --- | --- | --- |
| Composition | | |
| - Palladium wt % | 0.3 | 0.3 |
| - Alumina purity wt % | 99.5[(1)] | |
| - Sulfur wt % | 0.05 | — |
| Bulk density (kg/m$^3$) | 721 | 481 |
| Crush Strength (kg/m$^3$) | 256 | 80 |
| Surface Area (BET) m$^2$/g | 101 | 81 |
| Pore Volume cc/g | 0.56 | 0.21 |
| Acidity μmoles/g | | |
| Total | 93 | 20 |
| - Bronsted | 23 | 10 |
| - Lewis | 70 | 10 |

[(1)]Traces of impurities.

The three catalysts were tested under identical conditions using tubular reactors maintained under the same reaction conditions. 50 ml of each catalyst were used. The SCN feed employed has the following characteristics:

| | |
| --- | --- |
| Benzene | 78.5 wt % |
| Toluene | 3.0 wt % |
| Diolefins | 11.3 wt % |
| Olefins | 18.0 wt % |
| Saturates | 4.0 wt % |
| Bromine No. | 43.2 |
| UV (235μ) | 14.8 |

The feed was passed over the catalysts with hydrogen under the following conditions:

| | |
| --- | --- |
| LHSV | 4 |
| Hydrogen/Hydrocarbon ratio | 80 Nm$^3$/m$^3$ |
| Pressure | 25 bar g |
| Temperature | |
| - first 47 hours | 50° C. |
| - then | 80° C. |

Figure 3:
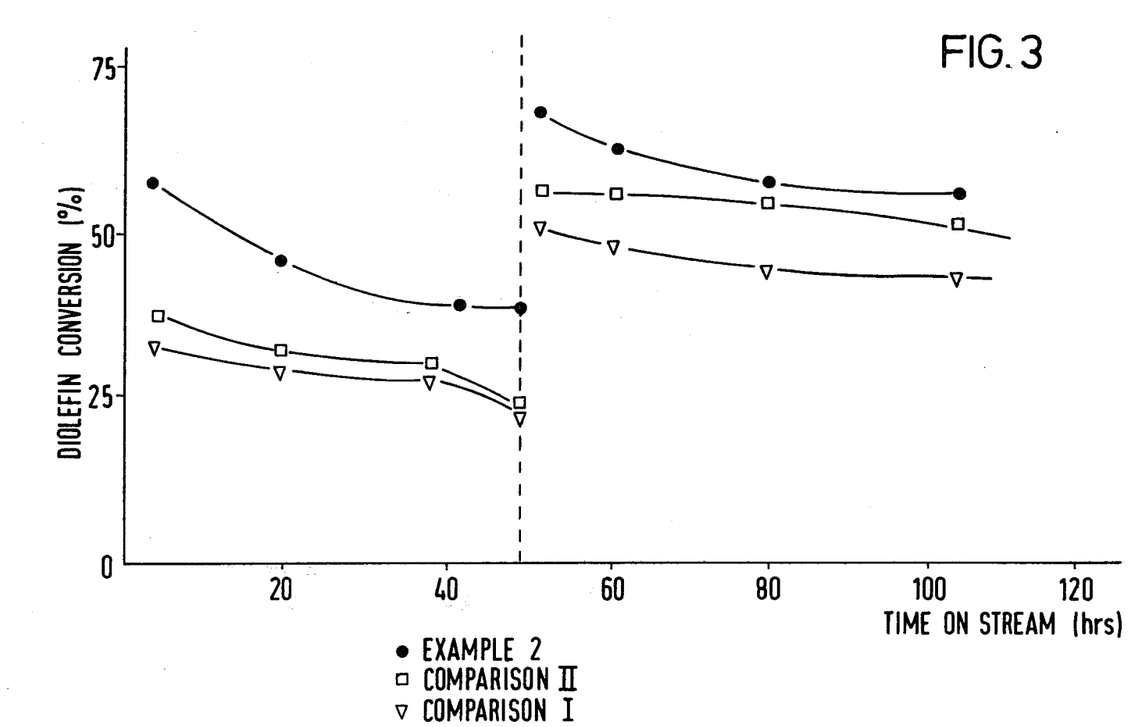
FIGS. 3 and 4 are similar graphs to FIG. 1, but showing the results for a supported palladium catalyst of the invention and for conventional catalysts using alumina supports.

Samples were taken every three hours, and the relative diolefin content was measured by the UVK method. The results are shown graphically in FIG. 3 as % diolefin conversion against time. It may be seen that, both at 50° C. and 80° C., the catalyst of the invention gives significantly greater degree of conversion, and this is maintained over the extended period of the testing. It is believed that the catalyst of the invention is subject to less fouling resulting from polymerisation.

EXAMPLE 9

Selective Hydrogenation-long term test

A similar investigation to that described in Example 8 was carried out over 150 hours.

Catalysts Tested

Example 2—supported palldium catalyst
Comparison I (see Example 5)
Comparison II (see Example 8)
Comparison III
    0.3 wt % palladium
    99.5 wt % alumina
    trace impurities
    bulk density—849 kg/m$^3$
    surface area (BET)=31 m$^2$/g
    bronsted acidity=8μ moles/g
    lewis acidity=9μ moles/g
    total acidity=17μ moles/g
SCN Feed substantially as Example 8

| Reaction Conditions | |
| --- | --- |
| Hydrogen/hydrocarbon ratio | 90 Nm$^3$/m$^3$ |
| Pressure | 25 bar g |
| LHSV | 6 |
| Temperature | 80° C. |

The temperature was selected to give diolefin conversions in the region of 50%±10% to enable differences in acidity to be observed. A higher temperature could be used in practical applications to secure a higher rate of conversion.

Results

Figure 4:
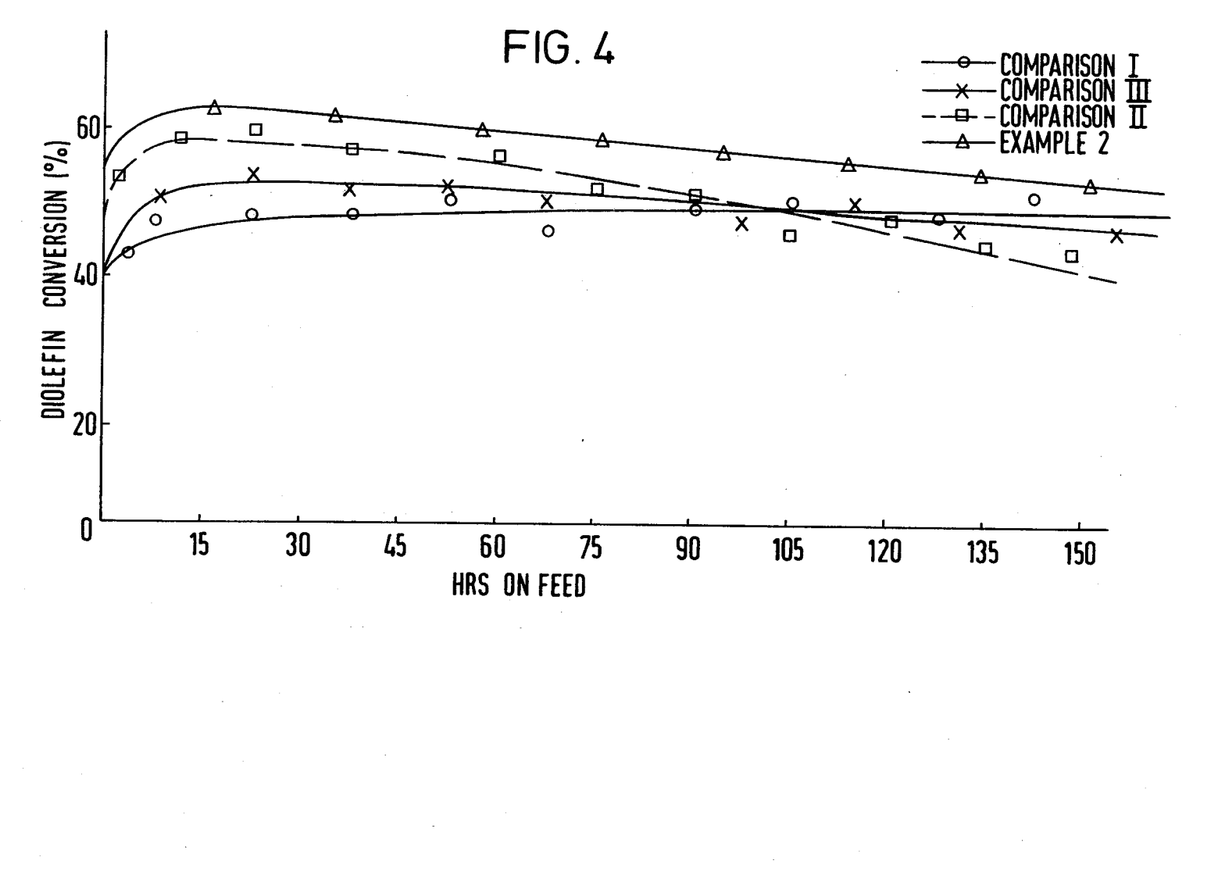

The results are shown graphically in FIG. 4. Again the UVK method was used to monitor diolefin conversion. The catalyst of the invention shows significantly greater activity which is maintained over the entire test. This indicates that the catalysts of the invention will be capable of greater run times between regenerations than conventional catalysts.

Comparative Testing—Acidity/Fouling Correlation

To investigate the relation between the acidity of a catalyst base and the long term fouling tendency of that base in hydrogenation reactions, hydrogenations were carried out using catalysts having supports with a range of acidities.

Silica polymorphs (prepared generally according to the procedure of U.S. Pat. No. 4,061,724 but containing sufficient aluminium to give total acidity outside the range specified for the invention) were impregnated with palladium. The palladium contents of each of the formed catalysts is given in Table 4, together with the total acidity measured by pyridine adsorption at 300° C. The catalysts were then used to hydrogenate an SCN-benzene heart cut over a 50 hour period isothermally under the following conditions.

| LHSV | 4 |
|---|---|
| Hydrogen/hydrocarbon | 80 Nm$^3$/m$^3$ |
| Pressure | 24 bar gauge |
| Temperature | |
| 0-12 hours | 25° C. |
| 12-30 hours | 50° C. |
| 30-50 hours | 80° C. |

The spent catalysts were then weighed to give the combined weight of catalyst, adsorbed material and fouling. The spent catalysts were first subjected to a vacuum of 10 mm Hg at 20° C. for 16 hours and reweighed, then heated successively to 100° C., 200° C., 300° C. and 450° C. in air, being held at each temperature for 16 hours and weighed. The vacuum treatment and heat treatment up to 200° C. removes unpolymerized, adsorbed hydrocarbons leaving the truly polymeric fouling which is removed by the 300° C. and 450° C. treatments. The results are shown in Table 4 in terms of % weight loss for each treatment and they demonstrate the link between catalyst acidity and fouling since as the total acidity is reduced the amount of fouling is also reduced. The results also demostrate that total acidity in excess of 40$\mu$ moles/g (as defined herein) results in significant amounts of true polymer fouling. The use of silica polymorphs with low acidity gives suprisingly high acidity and good acidity maintenance as demonstrated in the previous examples.

TABLE 4

| CATALYST | Pd wt % | acidity* | % wt loss after 16 hours at: | | | | | Fouling (wt %) |
|---|---|---|---|---|---|---|---|---|
| | | | 20° C. (Vacuum) | 100° C. | 200° C. | 300° C. | 450° C. | |
| A | 0.22 | 150 | 0.51 | 6.51 | 2.73 | 1.94 | 0.22 | 2.16 |
| B | 0.24 | 110 | 5.43 | 5.94 | 2.30 | 1.94 | 0.27 | 2.21 |
| C | 0.24 | 60 | 0.15 | 7.98 | 2.21 | 1.47 | 0.26 | 1.73 |
| D | 0.35 | 50 | 2.36 | 7.23 | 1.60 | 1.49 | 0.28 | 1.77 |

*total acidity: pyridine adsorption at 300° C. ($\mu$moles/g)

We claim:

1. A method of selectively hydrogenating a hydrocarbon feed to convert alkynes and dienes to alkenes containing a single olefinic double bond, which method comprises contacting the feed with hydrogen over a catalyst comprising palladium or platinum supported on a crystalline silica polymorph, said silica polymorph having, after calcination in air for at least one hour at 600° C., a mean refractive index of 1.39±0.01 and a specific gravity of 1.70±0.05, and said silica polymorph having a total acidity of not greater than 40$\mu$ moles/g as measured by pyridine adsorption at 300° C.

2. A method as claimed in claim 1, in which the silica polymorph has an X-ray powder diffraction pattern in which the six strongest d-values are:
 11.10±0.2 Å
 10.00±0.2 Å
 3.85±0.07 Å
 3.82±0.07 Å
 3.76±0.05 Å
 3.72±0.05 Å

3. A method as claimed in claim 1, in which the silica polymorph has, following calcination in air for at least an hour at 600° C. an adsorptive capacity for water vapour at 23° C. and a water vapour pressure of 4.6 mm Hg of less than 1 wt %, an infra-red spectrum which exhibits a substantial absence of absorption in the region 3700-3100 cm$^{-1}$ and an X-ray powder diffraction pattern containing at least the following d-values:
 11.10±0.2
 10.00±0.2
 9.75±0.1
 3.85±0.04
 3.82±0.04
 3.71±0.02
 3.62±0.02 and an absence of reflections intermediate the reflections corresponding to d-spacings of 3.82±0.04 Å and 3.71±0.02 Å.

4. A method as claimed in claim 1, in which the catalyst comprises from 0.05 to 1 wt % palladium.

5. A method as claimed in claim 4, in which the catalyst comprises from 0.1 to 0.5 wt % palladium.

6. A method as claimed in claim 1 in which the hydrogenation is carried out at a pressure of from 5 to 45 atmospheres and at an initial temperature of from 25° to 150° C.

7. A method as claimed in claim 1, in which the catalyst is prepared by impregnating formed silica polymorph with palladium.

8. A method as claimed in claim 7, in which the silica polymorph is contacted with an aqueous solution of a water-soluble palladium salt, dried and calcined to form palladium oxide thereon and the formed palladium oxide is then reduced to metallic palladium.

9. A method as claimed in claim 7 in which the silica polymorph is formed into pellets before impregnation.

10. A method as claimed in claim 1, in which the catalyst support contains less than 0.2 wt.% aluminium.

11. A method of selectively hydrogenating a hydrocarbon feed to convert alkynes and dienes to alkenes containing a single olefinic double bond, which method comprises contacting the feed with hydrogen over a catalyst comprising palladium or platinum supported on a crystalline silica having a structure analogous to a zeolite and having a total acidity of not greater than 40$\mu$ moles/g as measured by pyridine adsorption at 300° C.

12. A method as claimed in claim 11, in which the catalyst comprises palladium supported on the crystalline silica.

13. A method as claimed in claim 12, in which the catalyst comprises from 0.1 to 0.5 wt.% palladium.

14. A method as claimed in claim 11, in which the hydrogenation is carried out at a pressure of from 5 to 45 atmospheres, and at an initial temperature of from 25° to 150° C.

15. A method as claimed in claim 11, in which the crystalline silica has, after calcination in air for at least one hour at 600° C., a mean refractive index of 1.39±0.01 and a specific gravity of 1.70±0.05.

16. A method as claimed in claim 15, in which the crystalline silica has an X-ray powder diffraction pattern in which the six strongest d-values are:
11.10±0.2 Å
10.00±0.2 Å
3.85±0.07 Å
3.82±0.07 Å
3.76±0.05 Å
3.72±0.05 Å

17. A method as claimed in claim 15, in which the crystalline silica has, following calcination in air for at least one hour at 600° C., an adsorptive capacity for water vapour at 23° C. and a water vapour pressure of 4.6 mm Hg of less than 1 wt.%, an infra-red spectrum which exhibits a substantial absence of adsorption in the region 3700-3100 cm$^{-1}$ and an X-ray powder diffraction pattern containing at least the following d-values:
11.10±0.2 Å
10.00±0.2 Å
9.75±0.1 Å
3.85±0.04 Å
3.82±0.04 Å
3.71±0.02 Å
3.62±0.02 Å and an absence of reflections intermediate the reflections corresponding to d-spacings of 3.82±0.04 A and 3.71±0.02 A.

18. A method of selectively hydrogenating a hydrocarbon feed to convert alkynes and dienes to alkenes containing a single olefinic double bond, which method comprises contacting the feed with hydrogen over a catalyst comprising palladium or platinum supported on a crystalline silica comprising a highly siliceous zeolite with a tetrahedral silica framework within which the level of metal substitution is such that the total acidity of the silica is not greater than 40μ moles/g as measured by pyridine adsorption at 300° C.

19. A method as claimed in claim 18, in which the ratio of silicon to metal in the tetrahedral framework is greater than 5000.

20. A method as claimed in claim 18, in which the catalyst comprises from 0.1 to 0.5 wt.% palladium.

* * * * *